(12) United States Patent
Euser et al.

(10) Patent No.: US 8,183,410 B2
(45) Date of Patent: May 22, 2012

(54) PREPARATION OF FREE FLOWING GRANULES OF METHYLGLYCINE DIACETIC ACID

(75) Inventors: Huig Euser, Vlaardingen (NL);
Jean-Paul Janssens, Vlaardingen (NL);
Robert Jan Moll, Vlaardingen (NL);
Jerome Georges M. Sonjon,
Vlaardingen (NL)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 12/935,007

(22) PCT Filed: Mar. 31, 2009

(86) PCT No.: PCT/EP2009/053781
§ 371 (c)(1),
(2), (4) Date: Sep. 28, 2010

(87) PCT Pub. No.: WO2009/103822
PCT Pub. Date: Aug. 27, 2009

(65) Prior Publication Data
US 2011/0054215 A1     Mar. 3, 2011

(30) Foreign Application Priority Data
Apr. 1, 2008  (EP) .................................. 08153924

(51) Int. Cl.
*C07C 229/24* (2006.01)
*C11D 17/00* (2006.01)

(52) U.S. Cl. .......................... 562/571; 562/572; 510/442

(58) Field of Classification Search ........................ None
See application file for complete search history.

(56) References Cited

U.S. PATENT DOCUMENTS

| | | | |
|---|---|---|---|
| 3,956,379 A | 5/1976 | Beaver | 260/534 E |
| 5,981,798 A | 11/1999 | Schonherr et al. | 562/593 |
| 6,770,616 B1 * | 8/2004 | McGowan et al. | 510/446 |
| 2008/0045430 A1 * | 2/2008 | Witteler et al. | 510/218 |

FOREIGN PATENT DOCUMENTS

| | | |
|---|---|---|
| DE | 296 680 | 12/1991 |
| EP | 0 845 456 | 6/1998 |
| EP | 1 721 962 | 8/2008 |
| WO | 01/12768 | 2/2001 |
| WO | 2006/002954 | 1/2006 |
| WO | 2006/003434 | 1/2006 |

OTHER PUBLICATIONS

Kent et al, Powder Bulk Solids, Spray-Dryer Optimization, 2007, WWW.PowderBulkSolids.com, pp. 1-7.*
PCT International Search Report in PCT application PCT/EP2009/053781, 2009.
Abstract of DD 296 680 published Dec. 12, 1991.

* cited by examiner

*Primary Examiner* — Paul A Zucker
(74) *Attorney, Agent, or Firm* — Alan A. Bornstein

(57) ABSTRACT

The present invention concerns a process for the preparation of free flowing granules of low hygroscopicity of one or more methylglycine diacetic acid (MGDA) salts, of the formula wherein R=CH3 and M is hydrogen, alkali metal, alkaline earth metal, ammonium or substituted ammonium in the appropriate stoechiometric amounts, by a process comprising the steps of i) heating a concentrated slurry comprising methylglycine diacetic acid (MGDA) and/or any salts thereof, the slurry having a solids content in the range of 45% to 70% and suitably in the range from 50% to 70%, and a moisture content of 30% up to 55%, and suitably between 30% and 50%, to a temperature in the range of 50 to 120° C., preferably to about 80° C., and ii) spray granulating said slurry, using an air inlet temperature of 120° C. or less.

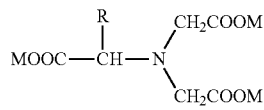

13 Claims, No Drawings

PREPARATION OF FREE FLOWING GRANULES OF METHYLGLYCINE DIACETIC ACID

TECHNICAL FIELD OF THE INVENTION

The present invention is in the field of the preparation of free flowing granules containing one or more salts of methylglycine diacetic acid (MGDA). More specifically, the invention encompasses the preparation of free flowing granules of one or more salts of methylglycine diacetic acid (MGDA) with low hygroscopicity, and the use thereof, in particular in machine dishwash detergent compositions.

BACKGROUND TO THE INVENTION

Amino polycarboxylic compounds such as methylglycine diacetic acid (MGDA) and variants thereof e.g. NTA (nitrile triacetic acid), GDA (glutamic diacetic acid), DPA (dipicolinic acid) and IDS (imino disuccinic acid) are suitable compounds for use as builder material in detergent compositions. The use thereof is however, in most cases restricted to their use in liquid applications. This is due to the fact that these materials in solid form tend to be hygroscopic and, on storage under ambient conditions, show an unacceptably reduced flowability. Such a restricted flowability is also considered a significant drawback on production of detergent compositions.

Particles of MGDA made via conventional spray drying processes tend to be fine and dusty, have a high tendency to absorb water at ambient conditions and loose their free-flowiness. The resulting products are hygroscopic, resulting in sticky powder and even in lumps. Different routes have been developed for preparing solids from solutions of glycine-N,N-diacetic acid derivatives were these drawbacks are overcome.

U.S. Pat. No. 3,956,379 describes a process in which a concentrated slurry of NTA is spray dried at very high temperatures. This has been found to result in porous and friable products.

DD 296 680 discloses the spray-granulation of saturated solution of NTA. The example discloses a solution which is well below the saturation point of NTA. It has been found that the use of the saturated solution still results in products with very poor hygroscopicity.

In EP 845456, the crystallisation of a very concentrated composition of the glycine-N,N-diacetic acid derivatives, containing between 10 and 30% moisture is described. By this process large particles with low hygroscopicity and good flowability can be obtained. However, this process requires dedicated equipment, and the low moisture composition has been found to be very difficult to process. Consequently, such a process is quite expensive.

SUMMARY OF THE INVENTION

In one embodiment, it is the object of the invention to provide for a process for preparing free flowing granules of low hygroscopicity comprising glycine-N,N-diacetic acid derivatives of the formula

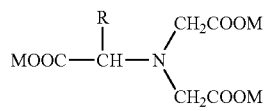

wherein
R=CH3 and M is hydrogen, alkali metal, alkaline earth metal, ammonium or substituted ammonium in the appropriate stoechiometric amounts. Preferably, M is sodium.

In this embodiment, free flowing granules comprising methylglycine diacetic acid (MGDA) or salts thereof are prepared. It has been found that this particular glycine-N,N-diacetic acid derivative provides very good performance as builder material in detergent compositions, in particular in machine dishwash detergent compositions.

Accordingly, in a second embodiment of this invention the use of such free flowing granules in detergent compositions is proposed, more in particular in machine dishwash detergent compositions.

In a further embodiment, the use of such free flowing granules for preparation of detergent tablets is proposed.

DETAILED DESCRIPTION OF THE INVENTION

We have now found a method for the production of granules containing or consisting of methylglycine diacetic acid salt (MGDA) by which free flowing MGDA particles can be obtained of any granule size—granule size usually being in the range of 50-2000 μm—as desired, of uniform size if so desired, and of which the particles do not lead to hygroscopicity and have a good friability resistance.

The process as such is readily available in the industry, and process conditions are easily applied. Moreover, it has been observed that the granules of the invention are advantageous compared to MGDA powder prepared by a conventional method such as spray drying, as the hygroscopicity is significantly reduced. Furthermore, granules of the invention have been found to be advantageous when compared to the granules prepared by the method of EP845456, when applied for the production of detergent tablets. In particular, it was found that the forces needed for pressing tablets can be reduced. Accordingly, tablets of good strength can be prepared applying lower tabletting forces when compared to forces used for preparing tablets using MGDA granules produced according to the prior art.

In the specification the word hygroscopicity is not only used to describe the phenomenon of the tendency to absorb water, but also the tendency to become sticky. In this specification, the granules are referred to as being of sufficiently low hygroscopicity if, on open storage under normal ambient conditions, e.g. 20° C. and a relative humidity of 65%, it retains its consistency as flowable granules over a period of at least one week.

Depending on the method of preparation of the methylglycine diacetic acid (MGDA) or its salts, its purity is usually found in the range of 70 to 99.9%, and preferably in the range of 80 to 99.9%, calculated on the dry matter content. When in this specification an amount of MGDA is indicated, material of such purity is meant unless indicated otherwise. Other components present are the impurities commonly formed in the production process of MGDA.

In this specification, where MGDA is referred to and is in its solid form such as powder, seed material or granules, a salt such as the sodium salt of MGDA, or a combination of salts is meant.

Particle size is measured by sieving. The mean particle size is calculated as the weight average.

In the specification, were a percentage is indicated weight percentage is meant unless indicated otherwise.

Thus, a process is found process for the preparation of free flowing granules of low hygroscopicity of one or more methylglycine diacetic acid (MGDA) salts, of the formula

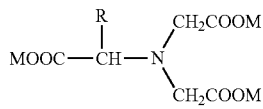

wherein

R=CH3 and M is hydrogen, alkali metal, alkaline earth metal, ammonium or substituted ammonium in the appropriate stoechiometric amounts, by a process comprising the steps of
  i) heating a concentrated slurry comprising methylglycine diacetic acid (MGDA) and/or any salts thereof, the slurry having a solids content in the range of 45% to 70% and suitably in the range from 50% to 70%, and a moisture content of 30% up to 55%, and suitably between 30% and 50%, to a temperature in the range of 50 to 120° C., preferably to about 80° C., and
  ii) spray granulating said slurry, using an air inlet temperature of 120° C. or less.

In a preferred embodiment, the concentrated slurry consists of methylglycine diacetic acid (MGDA) and/or any salts thereof.

In spray-granulation, it is the objective to spray the slurry onto existing seeds in the drying chamber and dry the slurry at that location so that the seeds grow to granules. Only when the granules reach a certain particle size the product is discharged from the equipment. This can be done batch wise, or even continuous.

The advantages found with the process of the invention are observed irrespective of whether the particles are prepared in a continuous or in batch process. The use of a continuous process has a number of advantages over the batch process and results in a further reduction of costs compared to other methods known for preparation of free-flowing granules of low hygroscopicity. Therefore, a continuous spray granulation process for the production of free-flowing MGDA (salt) granules is a preferred embodiment of this invention.

Where the use of a continuous process is envisaged, it is preferred that after the spray granulating the granules of a size larger than 200 μm, preferably larger than 300 μm and more preferred of about 400 μm or more are removed from the spray granulation equipment.

Removal of the granules of desired size can be done by a suitable method for continuous spray granulation, such as cyclone separation and filters or air classification. In a preferred embodiment, air classification is used for separating out the particles of the desired size. By adjustment of the air stream speed particles of (more than) a certain weight will fall down and are collected at the bottom of the equipment. Smaller particles are lifted up by the air stream to the cyclone and then back into the spray chamber.

Where a batch process is applied, the process further comprises
  iii) removing the granules formed during said spray granulation from the spray granulation equipment;
  iv) size separating the granules formed.

In this embodiment is also preferred to obtain larger granules and suitably, return the fines. In such an embodiment process may additionally comprise the steps of
  v) returning the particles of step iv) of a size <200 μm, preferably <300 μm, to the spray granulation tower for further spray granulation, and
  vi) collecting the granules of a size larger than 200 μm, preferably of larger than 300 μm, more preferred of about 400 μm or more
and optionally, removing the particles larger than 1200 μm.

Size separation can be done by any method known in the art and in particular when applying the batch process, is usually and suitably done by sieving.

The invention furthermore encompasses a process for preparing free flowing granules of low hygroscopicity containing methylglycine diacetic acid (MGDA) salt(s) of the formula indicated above, by the steps of any of the spray granulation processes described, and wherein the MGDA containing granules prepared have a mean particle size in the range of 350 μm to 750 μm, and preferably in the range of 450 μm to 750 μm.

Where the use of MGDA in a detergent composition is envisaged, it is highly desirable that the MGDA obtained by the process of the invention is dust free, and, in general, has an mean particle size in the range of 350 μm to 750 μm. It is preferred to adjust the particle size of the MGDA containing granules to the size of the further components used in the detergent composition. The granules obtained with the process of the invention are larger than 200 μm, and preferably larger than 300 μm, more preferred larger than 400 μm or even larger than 450 μm. Suitably, the granules are smaller than 1200 μm, more preferred smaller than 1000 μm and even more preferred smaller than 900 μm.

The preparation of granules which have a size in the range of 300 μm to 1000 μm is preferred. In an even further preferred embodiment the granules have a size in the range of 400 μm to 1000 μm, the mean particle size being in the range of 450 μm to 750 μm.

Certain applications may require even large particle sizes. In another embodiment of this invention, the granules have size in the range of 400 μm to 1000 μm, the mean particle size being in the range of 600 μm to 700 μm.

A preferred process includes the removal of granules of a size larger than 200 μm, preferably of about 300 μm or more from the spray granulation equipment, followed by sieving out the then collected granules having a mesh size of more than 1200 μm, preferably of more than 1100 μm, more preferred of more than 900 μm.

According to a preferred embodiment, free flowing methylglycine diacetic acid (MGDA) granules of the formula indicated above are prepared from a concentrated slurry having an MGDA content of at least 45%-70% and suitably from 50% to 70%, and a moisture content between 30% and 55%, and suitably between 30% and 50%.

When preparing a concentrated slurry from MGDA having an MGDA content of more than 50%, a fine, needle-like homogeneous crystal structure is formed. Such a slurry can be used as such for the spray granulation process and is preferred. In a particular suitable embodiment, the concentrated slurry has an MGDA content in the range of 55 to 65%.

When a slurry with an MGDA content in the range of 45-50% is applied also a fine, needle-like homogeneous crystal structure will be formed, for these amounts it is preferred that seed particles are present in said slurry, which will allow crystallisation and so, at the start of the spray granulation process sufficient seed granules are present. The granules are formed by spraying small quantities of the slurry onto seed particles while these are fluidised with the warm gas stream to evaporate the solvent from the liquid sprayed onto the seed particles. Also when a slurry with an MGDA content of more than 50% is applied seed particles can be applied. Where further ingredients are present in the slurry, also seed particles should be present in the slurry.

Preferably, the slurry is an aqueous slurry.

The concentrated slurry is heated to a temperature in the range of 50 to 120° C., and preferably to above 70° C., more preferred to about 80° C. It is furthermore preferred that the slurry is heated to a temperature of not more than 110° C., preferably less than 100° C.

In the spray granulation process, it is preferred to spray granulate the MGDA containing slurry at an inlet air temperature of up to 120° C. When applying higher temperatures, even at 130° C., the MGDA becomes sticky and such may result in serious problems during the processing, such as hot spots in the equipment. The maximum air temperature should be chosen be below the melting temperature of the material, whereas the minimum air temperature should be to chosen such that the solvent evaporates rapidly, suitably being on or above the boiling temperature of the solvent. Hence, where an aqueous slurry is applied, the inlet air temperature is preferably at least 100° C. Suitably, the inlet air temperature is in the range of 100 to 120° C. where an aqueous slurry is applied in the spray granulation process of the invention. In a further preferred embodiment of the invention, the inlet air temperature is less than 115° C., and more preferred in the range of 90 to 115° C.

The resulting particles are free flowing and have a low hygroscopicity. Free flowing in this context includes that particles are free flowing upon movement or handling. Preferably, the moisture uptake during the one week storage of the hygroscopicity test is less than 23%, further preferred less than 17%.

In the spray granulation process, the slurry feed stream is passed through a nozzle inside the spray dryer chamber, where it immediately comes into contact with a fluidizing gas stream at controlled temperature. The solvent evaporates rapidly and the resulting granules are separated from the air stream. Depending on the mode of operation of the equipment this separation can be done inside the fluidiser through a fluidiser classifier, or outside by sieving. The too fine particles are retained inside or returned to the fluidiser for further spray-granulation.

The production process furthermore allows for the preparation of granules comprising, in addition to MGDA salt, other (added) ingredients such as polymers, inorganic salts, and/or citrate or a combination thereof. Such granules are prepared from a slurry containing MGDA and/or any salts thereof, and any further ingredients as desired. This allows for a simplified production process of granules for a detergent composition. Suitable compounds can be selected from the composition the MGDA is intended to be used in. For example, when MGDA is intended to be used in a machine dishwash composition, the compounds can be selected from an ingredient suitably used in such a dishwash composition. Examples of compounds found to be suitable for use in the process of the invention are inorganic salts, such as carbonate, sulphate, silicate; organic salts, used e.g. as builders, such as citrate; or polymers, such as polyacrylates or sulphonated polymers. Mixtures of one or more of these compounds can be applied as well. These compounds are usually readily available as solutions and therefore allow for easy application in the current process, as such a solution can be mixed with a slurry containing MGDA and/or any salts thereof.

The resulting granules are homogeneous and, regardless of size, contain uniform proportions of the ingredients.

However, it has also been observed that such combination may lead to a reduction of hygroscopicity.

Preferably, in such an embodiment, the amount of further ingredients is therefore less than 25 wt %, preferably less than 20 wt % and even more preferred less than 15 wt %, based on the amount of MGDA. Also in this embodiment the process can be applied as a continuous process or batch process, the continuous process being preferred. The process allows for the preparation of granules having a size matching that of the further ingredients present in composition the granules will be used in, such is indicated above in this patent specification.

The resulting products in this process of the invention are found to show improved product stability, and, in particular, improved friability resistance.

The use of the free flowing granules obtained by the invention in detergent compositions been found to be very beneficial. In particular, the use of such granules in machine dishwash detergent compositions is proposed.

In a further embodiment, the use of such free flowing granules for the preparation of detergent tablets is proposed.

Friability test is carried out to determine the degree of disintegration of granules as a result of attrition during pneumatic transport. In this test, a current with a constant flow of 14.5 litres per minute is passed for 5 minutes through a sample from which particles larger than 1250 µm and smaller than 180 µm have been removed by sieving. The quantity of granulate (wt %) that has been broken into particles smaller than 180 µm is then determined. The result is calculated as follows:

$$\% \text{ attrition} = \frac{G-F}{G} \times 100$$

Where: G=quantity of sample used (about 25 g)

F=sieve fraction larger than 180 µm after the test.

The percentage attrition is expressed as % of raw material smaller than 180 µm after the test.

EXAMPLES

Example 1

On a laboratory scale, the following aqueous solutions were spray granulated

|  | A* | B |
|---|---|---|
| Moisture content (%) | 57 | 42 |
| MGDA (Trilon M) (%) | 43 | 58 |

*comparative example

The slurry of these compositions was heated to 50° C. for examples A and 85° C. for example B.

About 2 kg. of each of the compositions was spray granulated at an air inlet temperature of about 110° C. At the start a small quantity of MGDA powder was added as seed particles. The obtained products were removed and assessed.

The analysis of the resulting granules showed the following results:

|  | A | B |
|---|---|---|
| Appearance after storage** | Homogeneous gel | Free flowing |
| Moisture uptake** | 24% | 11% |
| Mean particle size | 270 μm | 360 μm |
| Friability (%) | 50 | 13.5 |

**when stored at 20° C. and 65% relative humidity for 1 week

As can be seen, both comparative examples suffered from poor hygroscopicity. Example B gives excellent low hygroscopicity, will also particle size and friability are significantly improved compared to the comparative example where the moisture content is more than 55% and the concentration of MGDA is below 45%.

Example 2

On a pilot plant scale, the following aqueous solutions were spray granulated

|  | C | D |
|---|---|---|
| Moisture content (%) | 42 | 45.5 |
| MGDA (Trilon M) (%) | 58 | 47 |
| Na-disilicate (anhydrous) (%) |  | 7.5 |

A throughput of about 30 kg/h was spray granulated. An inlet air of 105° C. for example C and 100° for example D was applied to fluidize the particles. The particles temperature in the bed was about 55° C. At the start a small quantity of MGDA powder was added as starting seed particles. An inlet air classification was applied in order to get the particles of mean size above 400 μm out.

A final throughput of about 20 kg/h was obtained and the granules were characterised. The analysis of the resulting granules showed the following results:

|  | C | D |
|---|---|---|
| Appearance after storage** | Free flowing granules | Slightly caked granules |
| Moisture uptake** | 13% | 19.5% |
| Mean particle size | 540 μm | 400 μm |
| Friability (%) | 2.0 | 2.1 |

The invention claimed is:

1. A process for the preparation of free flowing granules of low hygroscopicity of one or more methylglycine diacetic acid (MGDA) salts, of the formula

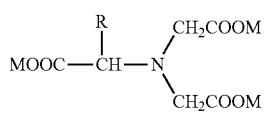

wherein
R=CH3 and M is hydrogen, alkali metal, alkaline earth metal, ammonium or substituted ammonium in the appropriate stoichiometric amounts, by a process comprising the steps of
i) heating a concentrated slurry comprising methylglycine diacetic acid (MGDA) and/or any salts thereof, the slurry having a solids content in the range of 45% to 70%, including seed particles of methylglycine diacetic acid and/or salts thereof with fine, needle-like homogenous crystal structure, and a moisture content of 30% up to 55%, to a temperature in the range of 50 to 120° C., and
ii) spray granulating said slurry, using an air inlet temperature of 120° C. or less.

2. Process according to claim 1, wherein after the spray granulating the granules of a size larger than 200 μm are removed from the spray granulation equipment.

3. Process according to claim 1, wherein the process further comprises
iii) removing the granules formed during said spray granulation from the spray granulation equipment;
iv) size separating the granules formed.

4. Process according to claim 3, wherein the process further comprises
v) returning the particles of step iv) of a size <200 μm to a spray granulation tower for further spray granulation, and
vi) collecting the granules of a size larger than 200 μm; and optionally, removing the particles larger than 1200 μm.

5. Process according to claim 1, wherein the concentrated slurry comprising methylglycine diacetic acid (MGDA) and/or any salts thereof furthermore comprises one or more further ingredients.

6. Process according to claim 5, wherein the amount of further ingredients is less than 15 wt %, based on the amount of MGDA.

7. Process according to claim 5, wherein the further ingredient is chosen from carbonate, sulphate, silicate, citrate, polyacrylates, sulphonated polymers, or mixtures thereof.

8. Process according to claim 1, wherein the concentrated slurry has a solids content in the range of 55 to 65%.

9. Process according to claim 1, wherein the inlet air temperature is less than 115° C.

10. Process according to claim 1, wherein the MGDA-salt containing granules prepared have a mean particle size in the range of 350 μm to 750 μm.

11. A process for preparing a detergent composition comprising the step of adding methylglycine diacetic acid (MGDA) salt(s) prepared according to the process of claim 1 to the detergent composition.

12. A process for preparing a machine dishwash detergent composition comprising the step of adding methylglycine diacetic acid (MGDA) salt(s) prepared according to the process of claim 1 to the machine dishwash detergent composition.

13. A process for preparing a detergent tablet comprising the step of adding methylglycine diacetic acid (MGDA) salt(s) prepared according to the process of claim 1 to the detergent tablet composition.

* * * * *